US012758278B2

(12) United States Patent
Niver

(10) Patent No.: US 12,758,278 B2
(45) Date of Patent: Oct. 13, 2026

(54) COMPRESSION DEVICE, KIT, AND METHOD

(71) Applicant: Medline Industries, LP, Northfield, IL (US)

(72) Inventor: Ryan Niver, Glenview, IL (US)

(73) Assignee: Medline Industries, LP, Northfield, IL (US)

( * ) Notice: Subject to any disclaimer, the term of this patent is extended or adjusted under 35 U.S.C. 154(b) by 144 days.

(21) Appl. No.: 18/800,214

(22) Filed: Aug. 12, 2024

(65) Prior Publication Data

US 2024/0398450 A1 Dec. 5, 2024

Related U.S. Application Data

(62) Division of application No. 17/975,717, filed on Oct. 28, 2022, now Pat. No. 12,102,362, which is a division of application No. 16/567,946, filed on Sep. 11, 2019, now Pat. No. 11,510,713.

(51) Int. Cl.
*A61B 17/80* (2006.01)
*A61B 17/86* (2006.01)

(52) U.S. Cl.
CPC ...... *A61B 17/8019* (2013.01); *A61B 17/8047* (2013.01); *A61B 17/8625* (2013.01); *A61B 17/866* (2013.01); *A61B 2017/8655* (2013.01)

(58) Field of Classification Search
CPC ........................ A61B 17/8047; A61B 17/8019
See application file for complete search history.

(56) References Cited

U.S. PATENT DOCUMENTS

| | | | | |
|---|---|---|---|---|
| 2009/0182383 A1* | 7/2009 | Prybyla ............. | A61B 17/8047 606/280 |
| 2018/0263669 A1* | 9/2018 | Peterson ........... | A61B 17/8605 |

* cited by examiner

*Primary Examiner* — Olivia C Chang
(74) *Attorney, Agent, or Firm* — Fitch, Even, Tabin & Flannery LLP

(57) ABSTRACT

A compression device made of a superelastic material having a peripheral portion with an upper surface, a lower surface, and a central opening extending therethrough is provided. One or more resilient teeth project inward of the peripheral portion into the central opening and are configured to exert a biasing force in an axial direction when deformed in a direction opposite the axial direction.

9 Claims, 13 Drawing Sheets

COMPRESSION DEVICE, KIT, AND METHOD

CROSS-REFERENCE TO RELATED APPLICATION

This application is a division of U.S. application Ser. No. 17/975,717, filed Oct. 28, 2022, which is a division of U.S. application Ser. No. 16/567,946 filed Sep. 11, 2019, now issued as U.S. Pat. No. 11,510,713, the disclosures of which are incorporated in their entireties by reference herein.

FIELD

This disclosure relates generally to orthopedic implants, and more specifically, to a compression device, kit, and method useful in orthopedic applications.

BACKGROUND

Washers are typically employed to help distribute load on an underlying structure upon insertion of a fastener, such as a screw. It is known to use washers in connection with threaded fasteners for orthopedic applications. For example, a washer may be used in connection with a bone screw and/or plate assembly to reduce the stress and load applied against the surface of a bone.

Lag screws are commonly used to repair bone fractures to compress joints or fracture sites in orthopedic applications. In use, an unthreaded proximal portion of the lag screw slides freely in a hole drilled through the bone on a proximal side of the joint or fracture site while a threaded distal end is screwed into an opposite side of the joint or fracture. As the screw is tightened, the threaded portion biases a distal region of the joint or fracture towards the proximal region to compress the joint or fracture site. Washers may be used in connection with such lag screws to reduce the stress on the proximal cortical bone due to such compression.

As a patient ambulates or as a fracture or joint heals, the compression provided by the lag screw may deteriorate. As a result of cyclic loading, gaps may form between the fractured bone segments thus interfering with the healing process. Maintaining compression in orthopedics across joints or fracture sites is desirable for healing.

It has now been found that a compression device composed at least in part of a superelastic material positioned between the head of a screw, optionally a lag screw, and a bone surface may exert a biasing force in an axial direction, as described in more detail hereinbelow, to assist in maintenance of compression.

DETAILED DESCRIPTION

Figure 1:
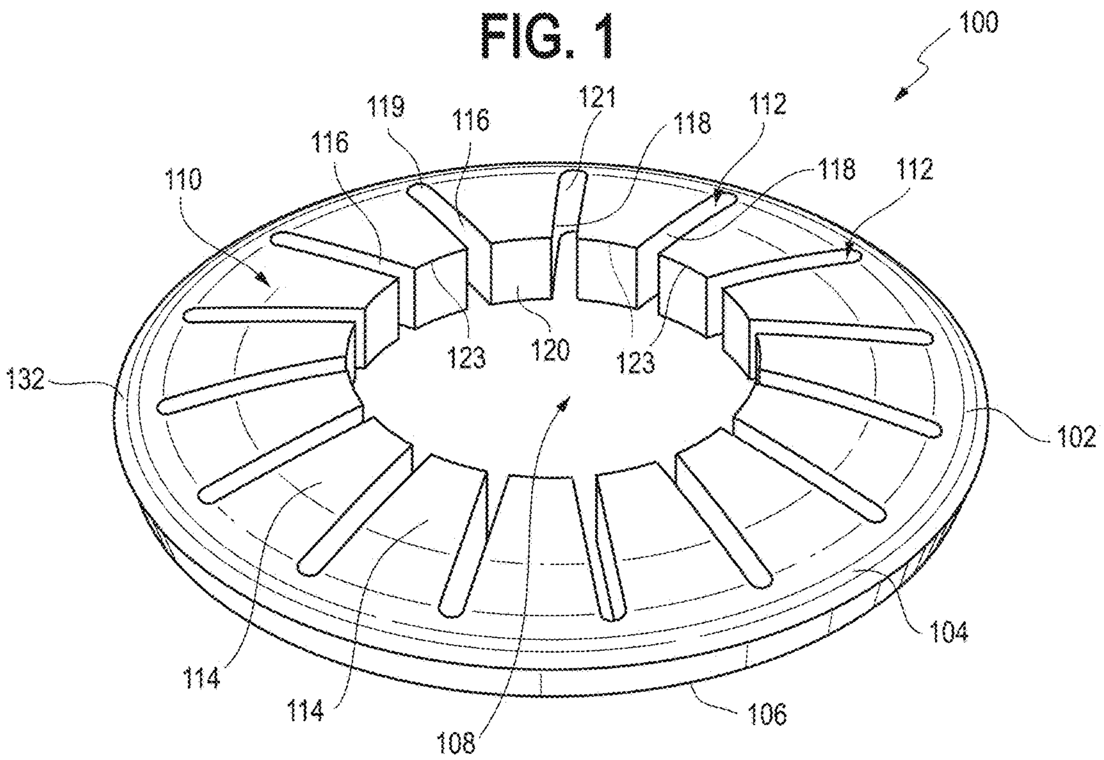
FIG. 1 is a perspective view of an exemplary compression device.

Generally, a compression device made of a superelastic material is provided. The compression device has a peripheral portion with an upper surface, a lower surface, and a central opening extending therethrough. One or more resilient structures such as a plurality of resilient teeth project inwardly into the central opening and are configured to exert a biasing force in an axial direction when deformed in a direction opposite the axial direction. The peripheral portion may be in the form of a generally annular ring and in some cases the ring may be a generally circular ring. In other forms the peripheral portion may have a generally square or triangular configuration.

When configured with resilient teeth, each tooth of the plurality of resilient teeth has a tip portion extending proximally beyond the upper surface of the peripheral portion such that the compression device is of a convex configuration in a resting state (i.e., before the resilient teeth have been deformed). The depth of the tip portion extending proximally beyond the upper surface of the peripheral portion may be adjusted to alter the force characteristics of the compression device, as discussed in further detail hereinafter. In other forms, each tooth has a tip portion extending distally beyond the lower surface of the peripheral portion such that the compression device is in a concave configuration. Similarly, the depth of the tip portion extending distally beyond the lower surface of the peripheral portion may be adjusted to alter the force characteristics of the compression device.

Likewise, the size, shape and number of resilient teeth, or other resilient member, may be adjusted to alter the force characteristics of the compression device. Each tooth may include a wedge-shaped projecting portion or projecting portion of any other appropriate shape such that an inferior portion of the tooth has a width greater than a superior portion thereof. In other forms, each tooth may include a cuboid-shaped projecting portion such that opposing sides of each tooth are substantially parallel one another. Likewise, the thickness of each tooth in a longitudinal direction may be consistent or may alternatively increase or decrease over a length thereof between the peripheral portion and a terminal end of each tooth.

The central opening of the compression device may be sized to receive a shaft portion of a fastener, such as a bone screw, therethrough such that the fastener may be received through the central portion and installed in a bone segment. A head portion of the fastener is configured to impinge upon the resilient teeth of the compression device such that the teeth of the compression device are deformed thereby. The superelastic resilient teeth exert a biasing force against the head portion of the fastener upon being deformed.

The compression device described above may be installed and seated directly against the cortex of a bone, or in alternative forms, a bone plate may be employed. In still other embodiments, the compression device may be at least partially countersunk in a bone segment. For example, a countersink tool (e.g., a drill) may be used to drill a countersunk bore in the bone segment sized to at least partially receive and seat the compression device therein. In some forms, peripheral edges of the compression device may contact and abut the surface of the bone segment, and the resilient teeth may be compressed inwards within the countersunk bore. A fastener may thereafter be advanced through the central opening of the compression device in the countersunk bore such that the head portion of the fastener compresses the resilient teeth thereof and remains flush with the cortex of the bone to reduce surrounding tissue irritation.

A kit including a compression device as described above and a countersink tool also may be provided. The countersink tool may include a drill or drill bit to be used to drill a countersunk bore to install the compression device in a segment of bone, the bore sized to at least partially seat the compression device therein. Optionally, the kit may include one or more fasteners such as bone screws.

The present disclosure further provides methods for installing the compression device into a bone segment. In one example, a bone segment of a patient may be surgically exposed and a guide wire may be advanced therein. A pilot hole may be cut into the bone segment to receive the shaft of a fastener therein, and thereafter, a countersunk bore may be cut into the bone segment. In some forms, the compression device may be placed around the shaft of a cannulated bone screw such that the bone screw and compression device may be advanced over the guide wire to insert the bone screw into the pilot hole. In other forms, the compression device provided herein may be placed in the countersink, and a bone screw may be advanced through the central opening of the compression device and into the pilot hole. As the bone screw is advanced, the head portion of the bone screw impinges upon, and compresses, the teeth of the superelastic compression device into the countersunk bore such that the teeth exert a biasing force against the head portion of the bone screw. In other methods, the compression device may be positioned immediately adjacent the cortex of the bone. In still other methods, a bone plate may be provided including a recessed opening sized to receive and seat the compression device at least partially therein. The compression device may be positioned in the opening and the bone plate may thereafter be secured to a bone segment.

Figure 2:
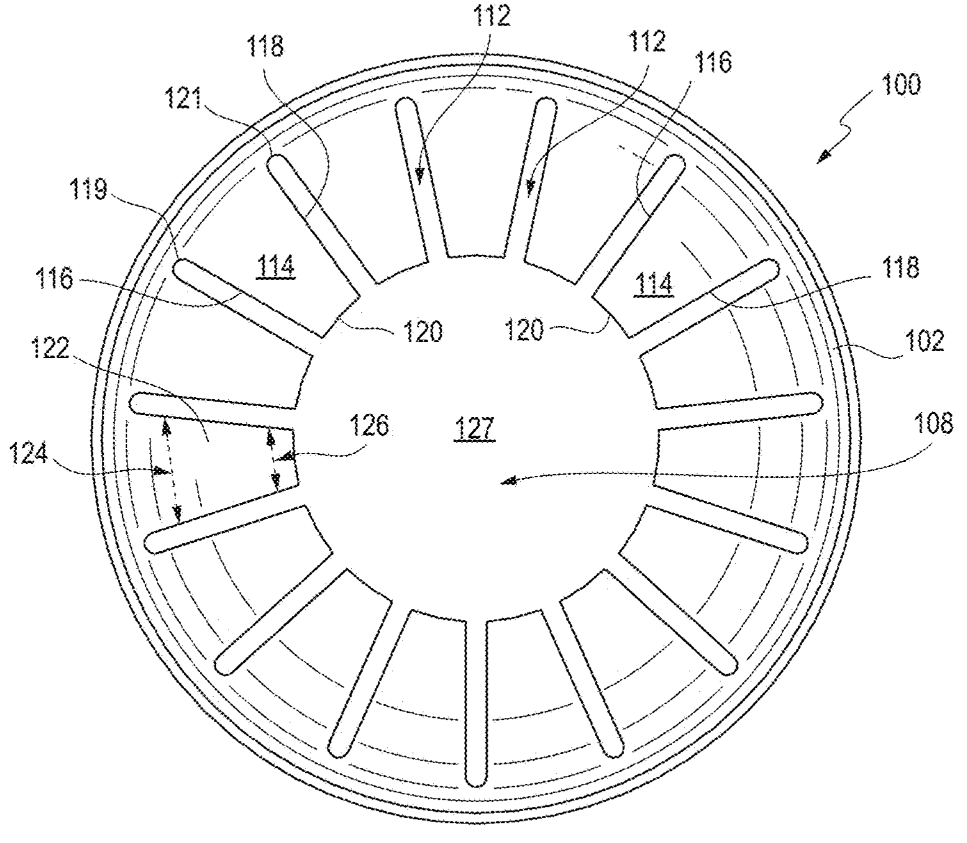
FIG. 2 is a top plan view of the compression device shown in FIG. 1.
Figure 3:
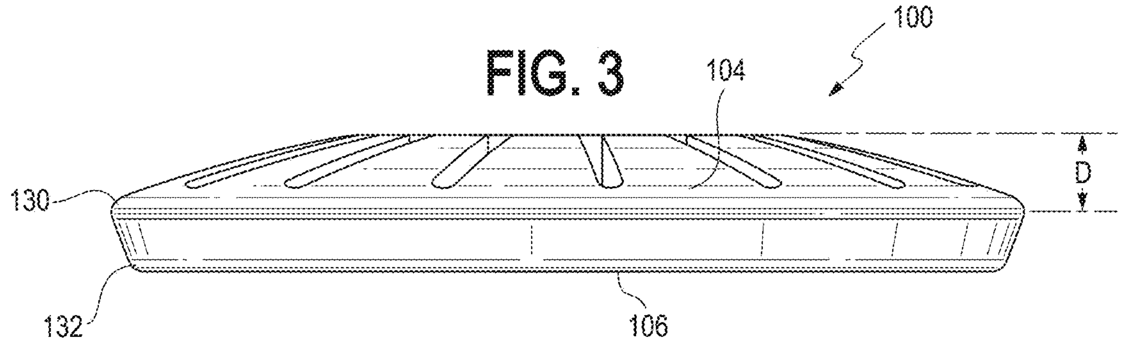
FIG. 3 is a side elevational view of the compression device shown in FIG. 1.

Referring now to the drawings, and more particularly FIGS. 1-3, an exemplary compression device 100 is provided including a peripheral portion 102 in the form of a generally annular ring having an upper surface 104, a lower surface 106, and a central opening 108 extending therethrough. As illustrated, a plurality of resilient teeth 110 project radially inwardly from the peripheral portion 102 into the central opening 108. The teeth 110 are spaced such that they define gaps 112 therebetween. By way of example, and for simplicity of reference to the drawings, the illustrated peripheral portion 102 is shown as a generally circular ring but the peripheral portion may, in other forms, be circular, oblong, square, triangular, or obround.

Each tooth 114 of the plurality of teeth 110 may include a first side edge 116, a second side edge 118, and a terminal edge 120. As illustrated in FIG. 2, each tooth 114 of the compression device 100 has a generally wedge-shaped portion 122 such that an inferior portion 124 of the tooth 114 has a width wider than a superior portion 126 of the tooth 114. So configured, the major part of the first side edge 116 of each tooth 114 is substantially parallel the major part of the second side edge 118 of an adjacent tooth 114 and, together with the cusps 119, 121, define a U-shaped gap 112 therebetween. In other forms, the teeth and gaps can have a variety of different shapes. For example, the teeth may have a substantially triangular profile such that the first and second side edges 116, 118 terminate at a single point as opposed to terminal edge 120, among other forms.

In addition, the peripheral portion 102 and plurality of teeth 110 may have a variety of different thicknesses. Depending on the shape of the teeth 110 and the thickness of the peripheral portion 102 and the teeth 110, different force characteristics may be imparted to the compression device. For example, in some forms, each tooth may reduce in thickness along a length thereof between the inferior portion and the superior portion. In other forms, the thickness of each tooth may remain consistent along the length thereof between the inferior portion and superior portion.

The configuration of the teeth will affect the axial force exerted upon compression of the teeth by the head of a bone screw or other fastener.

As illustrated in FIGS. 1-3, the terminal edge 120 of each tooth 114 of the compression device 100 is contoured such that the terminal edges 120 of the teeth 110 define a major opening 127 within the central opening 108. The major opening as illustrated is generally defined by the rounded terminal edges 120 of each of the teeth, and in other forms, could be defined by terminal edges formed in other shapes. In one example form, the opening 127 defined by the terminal edges 120 of the teeth 110 has a diameter of about 7.5 mm (as measured based on a completed circle defined by completing the terminal edges 120 of the teeth), and the peripheral portion 102 has a diameter of about 15 mm. In other forms, the diameters of the opening 127 and the peripheral portion 102 may vary for different surgical procedures, or when the compression device 100 is used in connection with a bone plate as described in further detail below.

Additionally, the peripheral portion 102 of the compression device 100 may include chamfered or filleted edges (e.g., filleted edges 130, 132), as shown most clearly in FIG. 3, to inhibit or reduce irritation to surrounding tissue when the compression device 100 is installed adjacent a bone segment.

As described above, at least the resilient teeth and preferably the entire the compression device 100 is formed of a superelastic material, generally a metal alloy such as a nitinol alloy, which is a family of nickel-titanium alloys. The plurality of resilient teeth 110 will thereby exert a biasing force in an axial direction when deformed in an opposing axial direction, by which is contemplated a biasing force having an axial component. Superelasticity is a well-recognized phenomenon of certain alloys in which the material deforms reversibly in response to an applied stress. In some forms, the compression device material should be superelastic at both ambient temperatures (e.g., about 25° C.) and the normal body temperature of the intended patient, which, in the case of human patient, is in the range of about 36° to 38° C. In other embodiments, alloys that are not superelastic at ambient temperature but that become superelastic at body temperatures may be employed.

As illustrated, the compression device 100 is in a generally convex or dome-shaped configuration in its resting state before any force has been applied thereto. As seen most clearly in FIG. 3, the resilient teeth 110 extend radially inwards about the peripheral portion 102 in an arcuate configuration superior the upper surface 104 thereof at a depth D. In other words, a tip portion 123 of the teeth 110 extends proximally beyond the upper surface 104 of the peripheral portion 102. The depth D can be any suitable depth depending on the selected application and the desired force characteristics of the compression device 100. An exemplary range for depth D is from about 0.25 mm to about 1.0 mm. The selected depth can depend on a variety of factors, including the geometry of the teeth 110, the shape of the teeth 110, and the desired force characteristics of the compression device 100. In other forms, the depth D may be equal to about 0 mm such that the compression device 100 is substantially flat in the resting state, and a tip portion of the teeth 110 does not extend proximally beyond the upper surface 104 or distally beyond the lower surface 106, as discussed below with respect to FIG. 17. In still other forms, the resilient teeth 110 may extend radially inwards about the peripheral portion 102 in an arcuate configuration distal of the lower surface 106 thereof such that the compression device 100 is of a concave or bowl-shaped configuration, as discussed below with respect to FIG. 18. In further forms, a tip portion of a first number of teeth 110 may extend proximally beyond the upper surface 104 and a second number of teeth 110 may extend distally beyond the lower surface 106.

As shown, the plurality of teeth 110 of compression device 100 includes 15 teeth. However, the plurality of teeth 110 may include any number of teeth extending radially inward from the peripheral portion 102 of the compression device 100, including a single tooth in some forms. Although the teeth 110 shown in FIG. 2 are spaced equally about the peripheral portion 102 of the compression device 100, the teeth 110 may be arranged in different configurations with different spacing. Such different configurations and different numbers of teeth 110 may impart different force characteristics to the compression device 100 such that the resilient teeth may exert a stronger or weaker biasing force upon depression thereof.

The compression device 100 provided herein is configured to be used in connection with a variety of different fasteners, including threaded fasteners such as cannulated bone screw 128 illustrated in FIGS. 4-7. In other forms, nails for use in orthopedic applications or other suitable fasteners may be employed. The illustrated bone screw 128 is a lag-type bone screw commonly used for fixation or stabilization of one or more bone segments and includes a head portion 134, a shaft 138 having a proximal portion 140 configured to slide freely in a hole drilled through bone on a near side of the joint or fracture site, and a threaded distal end 142 configured to be screwed into an opposite side of the joint or fracture. In other forms, the bone screw 128 may be a fully threaded screw.

The shaft 138 is sized to fit within the major opening 127 of the compression device such that it is not impeded by the teeth. As the screw 128 is advanced into a bone segment, the head portion 134 of the screw 128 may contact the resilient teeth 110 of the compression device 100 proximate the near side of the bone while the threaded distal end 142 pulls the opposite side of the joint or fracture towards the near side to compress the fracture site. In some forms, the fastener such as bone screw 128 may be osseointegrating and may be formed of titanium or an alloy thereof, or may be formed of other biocompatible osseointegrating materials. In other forms, the fastener could be formed of bioresorbable materials such as poly-L-lactic acid (PLLA), polyether ether ketone (PEEK), among others.

Figure 4:
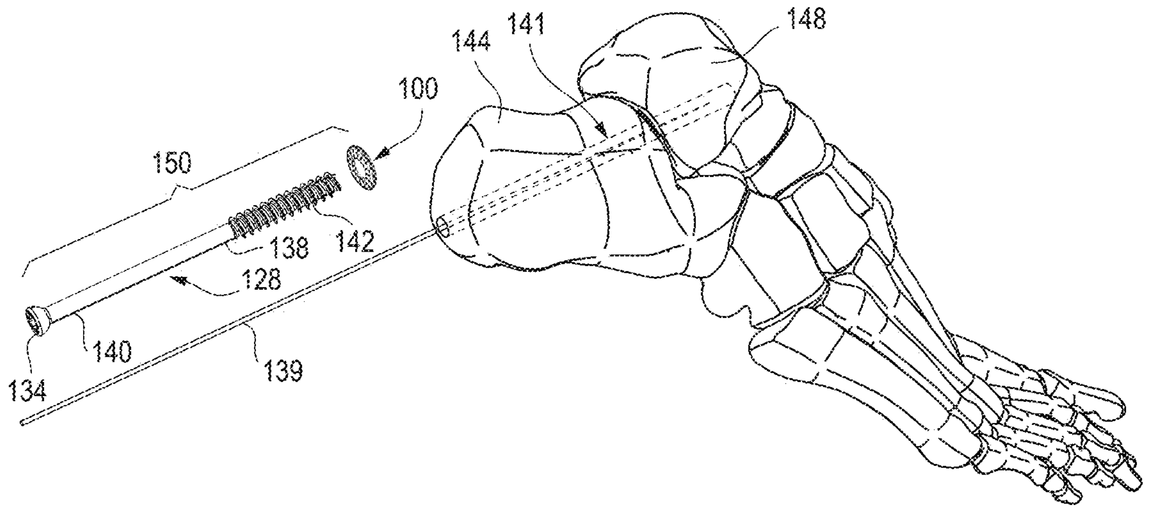
FIG. 4 is a view illustrating a cannulated lag-type bone screw, the compression device of FIG. 1, and a surgical region of a patient's calcaneus showing a guide wire inserted into the calcaneus with a pilot bore drilled therein.
Figure 5:
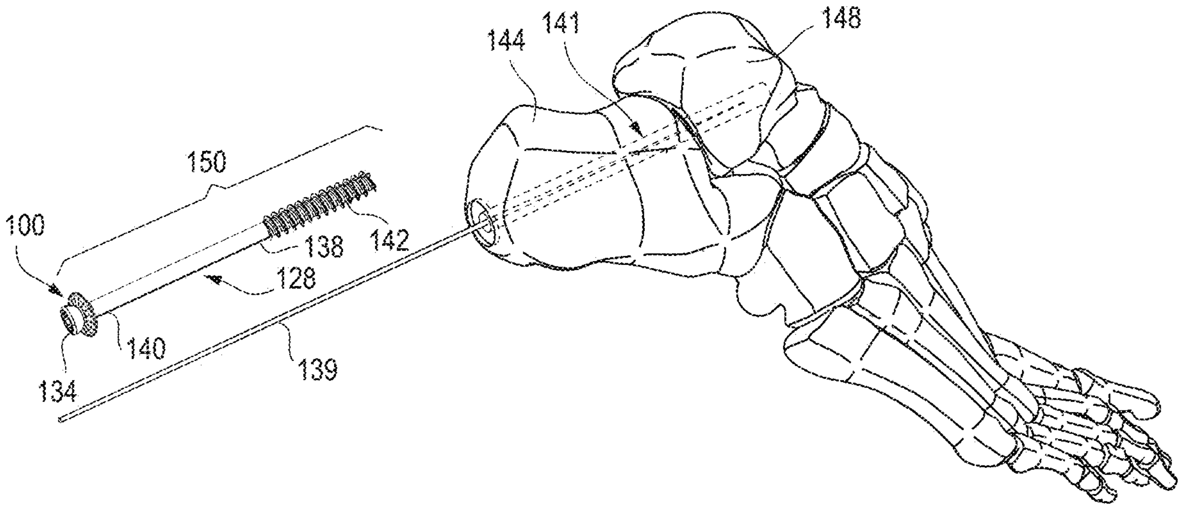
FIG. 5 is a perspective view of the surgical region of the patient's calcaneus as shown in FIG. 4 with a countersunk bore therein.

FIG. 4 illustrates an exemplary initial step for installation of cannulated bone screw 128 and compression device 100 in a patient's calcaneus 144. As shown a guide wire 139 is inserted into the calcaneus 144 and through a portion of the talus 148. A cannulated drill bit may advance along the guide wire to drill a pilot hole 141 for receiving the shaft 138 of the screw 128. As shown in FIG. 5, while the guide wire 139 is still inserted, a countersink tool having a drill bit (e.g., countersink tool shown in FIG. 23) may be used to drill the countersunk bore 146 that is sized to at least partially receive the compression device 100 and the head portion 134 of the bone screw 128 therein once installed. In addition, the compression device 100 may be positioned to surround the shaft 138 of the cannulated bone screw 128 proximate the head portion 134 such that both may be received over the guide wire 139 for installation as described below.

Figure 6:
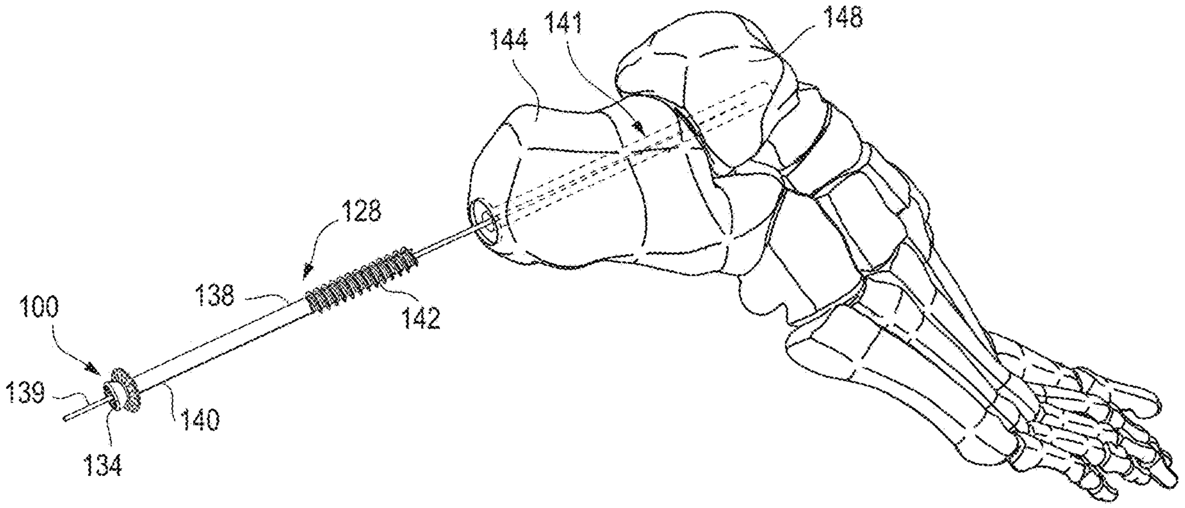
FIG. 6 is perspective view of the surgical region of the patient's calcaneus as shown in FIG. 4 showing the cannulated bone screw and compression device received over the guide wire and aligned with the countersunk bore.
Figure 7:
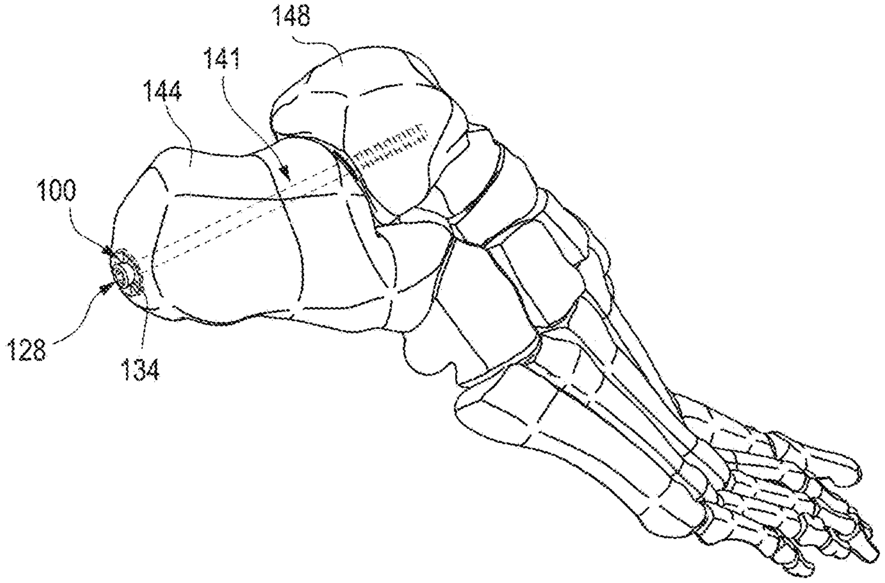
FIG. 7 is a perspective view depicting the surgical region of FIG. 6 after installation of the bone screw into the calcaneus and deformation of the compression device, and after the guide wire has been removed.

With respect to FIG. 6, the cannulated screw 128 and compression device 100 are shown aligned with the patient's calcaneus 144 and received along the guide wire 139 such that the compression device may be seated at least partially in the bore 146 and the screw may be advanced into the pilot hole 141. Thereafter, as shown in FIG. 7, the guide wire 139 is removed and the bone screw 128 is advanced into the calcaneus 144 such that the threaded distal end 142 of the screw 128 is advanced into the talus bone 148. The head portion 134 of the screw 128 impinges upon the teeth 110 of the compression device 100 and deforms the teeth 110 while the superelastic, resilient teeth 110 exert a biasing force in an opposite direction against the head portion 134 of the screw 128 to maintain compression between the calcaneus and the talus bones 144, 148. As illustrated, the teeth 110 of the compression device 100 are compressed into a flat configuration, and may further be compressed such that the compression device 100 is of a concave configuration with the teeth 110 deformed inwardly within the countersunk bore 146 due to impingement of the head portion 134 of the screw 128. The countersunk bore 146 may be sized such that upon compression of the compression device 100, the head portion 134 of the bone screw 128 is flush with the surface of the bone segment. In other words, the compression device 100 creates a constant biasing force under the head portion 134 of the bone screw 128 such that the resilient teeth 110 generate sustained compression between the calcaneus 144 and the talus 148.

In use, the compression device 100 is typically provided in the form of a kit including one or more compression devices 100 and a countersink tool (shown in FIG. 23) for drilling a countersink in a segment of bone. Optionally, the kit may also include a guide wire (e.g., guide wire 139). In other forms, the compression device 100 may be provided with a fastener such as bone screw 128 (e.g., kit 150 shown in FIG. 4). In some forms, an implant manufacturer may provide several sizes or shapes of compression devices or fasteners to accommodate various patients and types of procedures.

Figure 8:
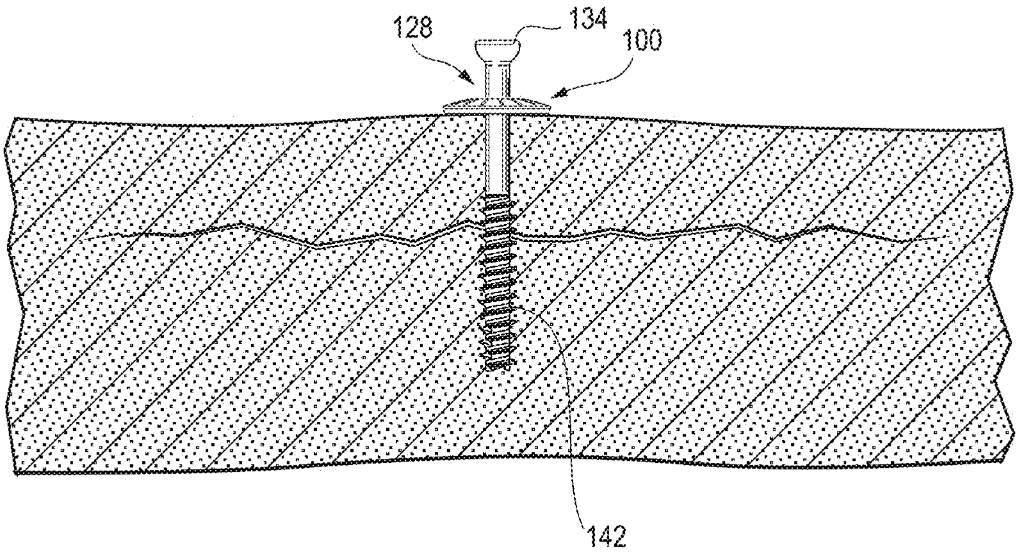
FIG. 8 is a cross-sectional view of a bone section of a patient into which a bone screw has been inserted during the process of advancing the bone screw but prior to impingement of the head of the bone screw on the compression device.
Figure 9:
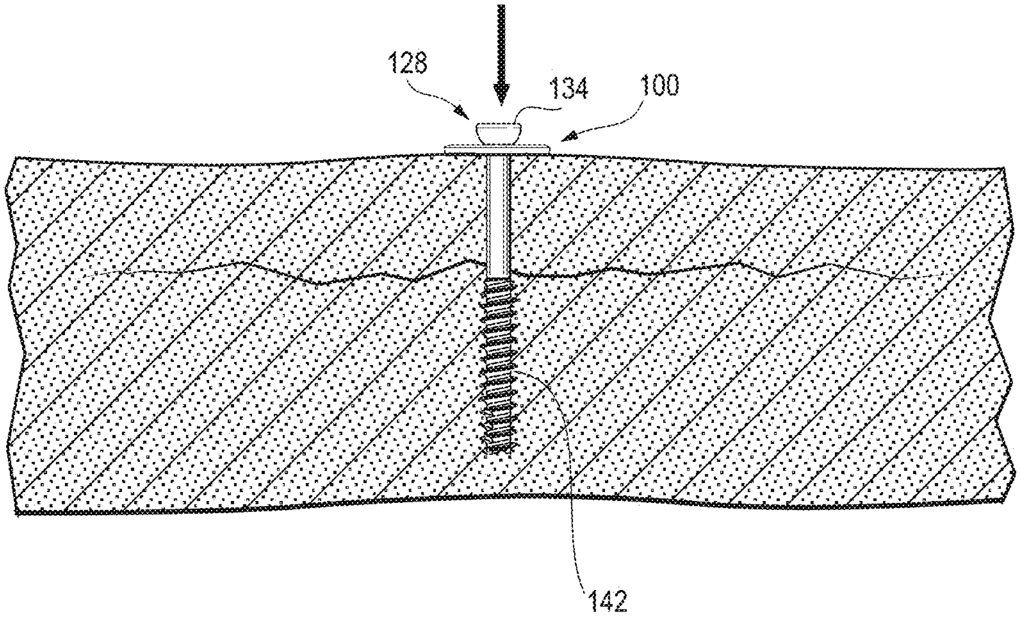
FIG. 9 is a cross-sectional view of the bone section shown in FIG. 8, at a further point during the process of advancing the bone screw and illustrating impingement of the head of the bone screw on the compression device.

With respect to the fractured bone segment depicted in FIGS. 8 and 9, an alternative use of the compression device 100 is shown. As illustrated in FIG. 8, compression device 100 has been positioned immediately adjacent the cortex of the bone segment and has not yet been compressed by the head portion 134 of the screw 128. The bone screw 128 is being advanced downwards through a pre-drilled bore into the bone segment such that the threaded distal portion 142 is inserted into the far portion of the fracture to compress the two fractured portions of bone.

FIG. 9 depicts a further point during the process of advancing the bone screw 128 and illustrating the impingement of the head portion 134 of the bone screw 128 on the resilient teeth 110 of the compression device 100. As shown, the threaded distal portion 142 of the screw 128 has been inserted into the far portion of the bone and the screw 128 is stabilizing the two fractured portions of bone. In addition, the resilient teeth 110 of the compression device 100 are now compressed and exert a biasing force upwards on the head portion 134 of the screw 128 to maintain such compressive force between the fractured bone segments. Even if patient ambulation or other factors disturb the compression of the bone segments imparted by the screw 128, the biasing force exerted by the resilient teeth 110 promotes continued compression. Although the bone screw 128 is shown advancing into the bone segment at an angle approximately transverse the surface of the bone, the bone screw 128 could also be advanced through the bone segment at an angle such that the resilient teeth 110 of the compression device 100 would still impart a biasing force having an axial component.

Figure 10:
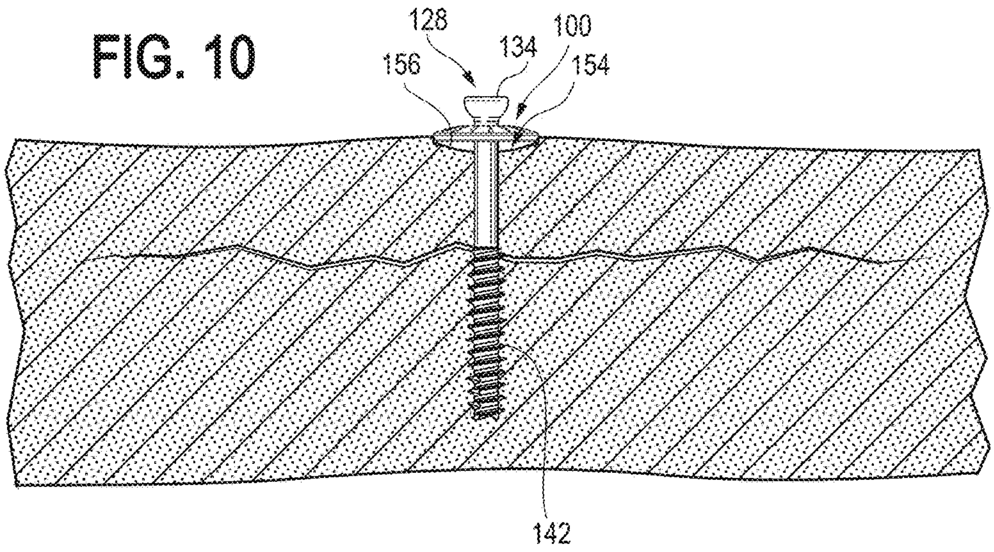
FIG. 10 is a cross-sectional view of a bone section of a patient with a compression device seated in a countersunk bore thereof during the process of advancing the bone screw but prior to impingement of the head of the bone screw on the compression device.
Figure 11:
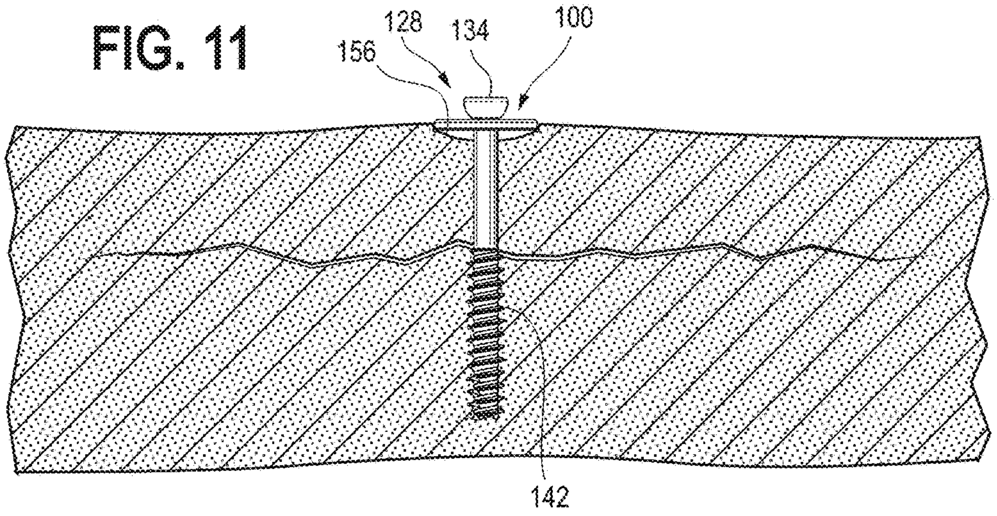
FIG. 11 is a cross-sectional view of the bone section shown in FIG. 10, at a further point during the process of advancing the bone screw and illustrating impingement of the head of the bone screw on the compression device.
Figure 12:
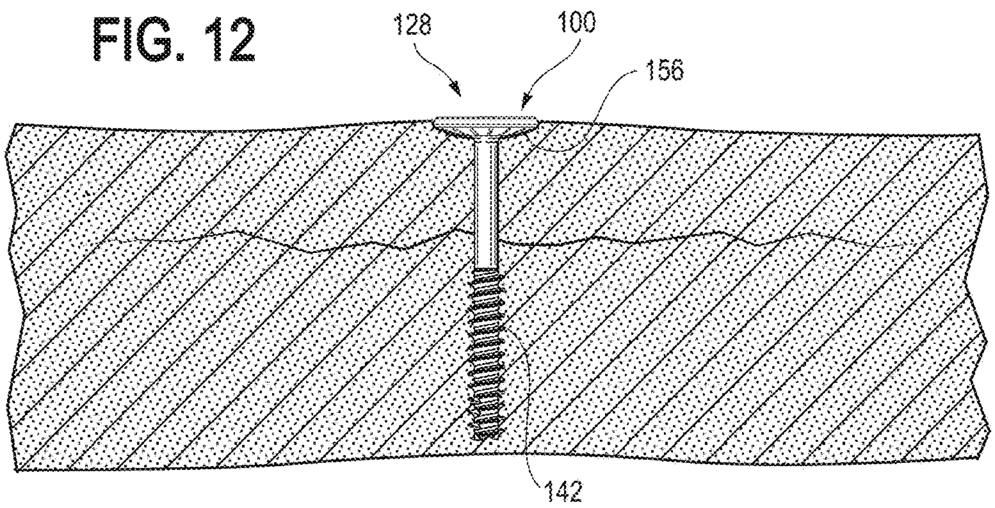
FIG. 12 is a cross-sectional view of the bone section shown in FIG. 10, at a final point during the process of advancing the bone screw and illustrating impingement of the head of the bone screw on the compression device.

Alternatively, the compression device 100 and screw may be countersunk as shown in FIGS. 10, 11 and 12. In these Figures a bone screw 128 is configured to be positioned adjacent a bore 152 sized to at least partially receive the compression device 100, or resilient teeth 110 thereof, within. As illustrated in FIG. 10, compression device 100 has been positioned proximate the countersunk bore 152 with edges thereof contacting the surface of the bone, and the device 100 and has not yet been compressed by the head portion 134 of the screw 128. The bone screw 128 is being advanced downwards through the bone segment such that the threaded distal portion 142 is inserted into the far portion of the fracture to compress the two fractured portions of bone. As illustrated, a distal portion 154 of the bore 152 includes a concave surface 156 (e.g., as drilled via the countersink tool shown in FIG. 23) such that the compression device 100 may be fully compressed thereon as shown more clearly in FIG. 12, and the head portion 134 of the screw 128 may be positioned substantially flush with the surface of the bone. In other forms, the distal portion 154 of the bore 152 is of a generally flat surface such that the teeth 110 of the compression device 100 may be compressed thereagainst.

FIG. 11 illustrates a further point during the process of advancing the bone screw 128 and illustrating the impingement of the head portion 134 of the bone screw 128 on the resilient teeth 110 of the compression device 100. At this point, the head portion 134 has compressed the resilient teeth 110 of the compression device 100 such that the device 100 is deformed into a flat configuration.

FIG. 12 illustrates a final point during the process of advancing the bone screw 128, showing the resilient teeth 110 of the compression device 100 fully compressed inwardly within the bore 152 by the head portion 134 of the bone screw 128 such that the compression device 100 is of a concave configuration and the teeth 110 are abutting concave surface 156. At this point, the head portion 134 is received within the bore 152 such that it is substantially flush with the surface of the bone and the threaded distal portion 142 has been inserted into the far portion of the bone such that the screw 128 compresses the two fractured portions of bone. In addition, the resilient teeth 110 of the compression device 100, now compressed into a concave configuration, exert an axial biasing force on the head portion 134 of the screw 128.

Figure 13:
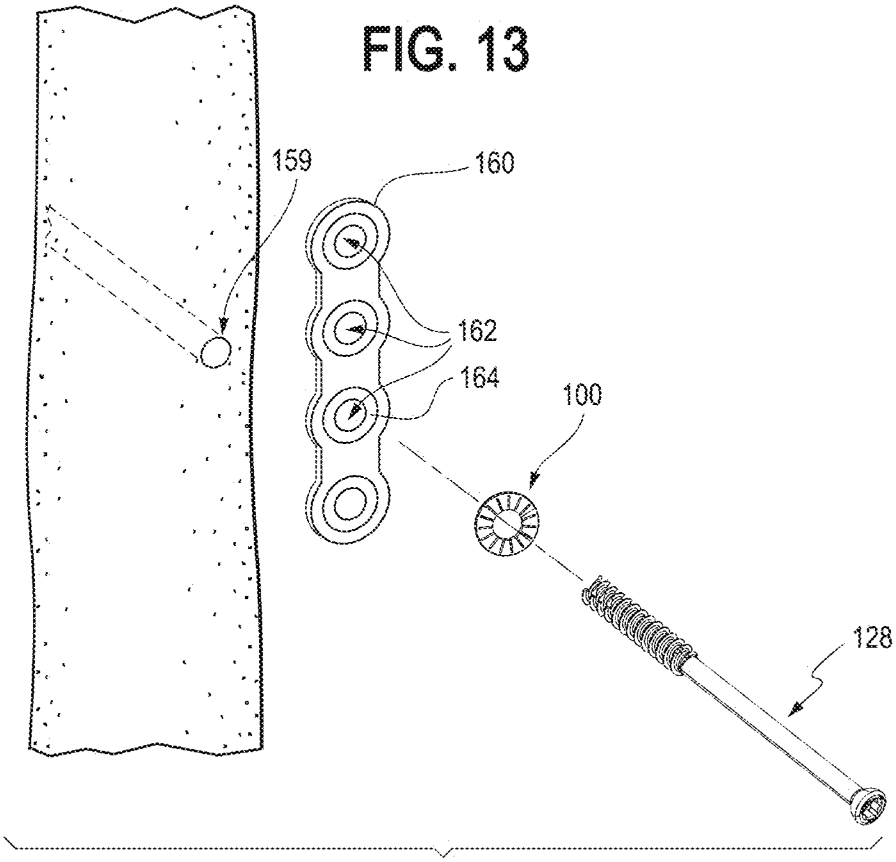
FIG. 13 is a view illustrating a lag-type bone screw, the compression device of FIG. 1, a bone plate, and a surgical region of a patient's bone, the Figure illustrating the relative positioning of the screw, bone plate, compression device, and bone prior to insertion of the screw into the bone.
Figure 14:
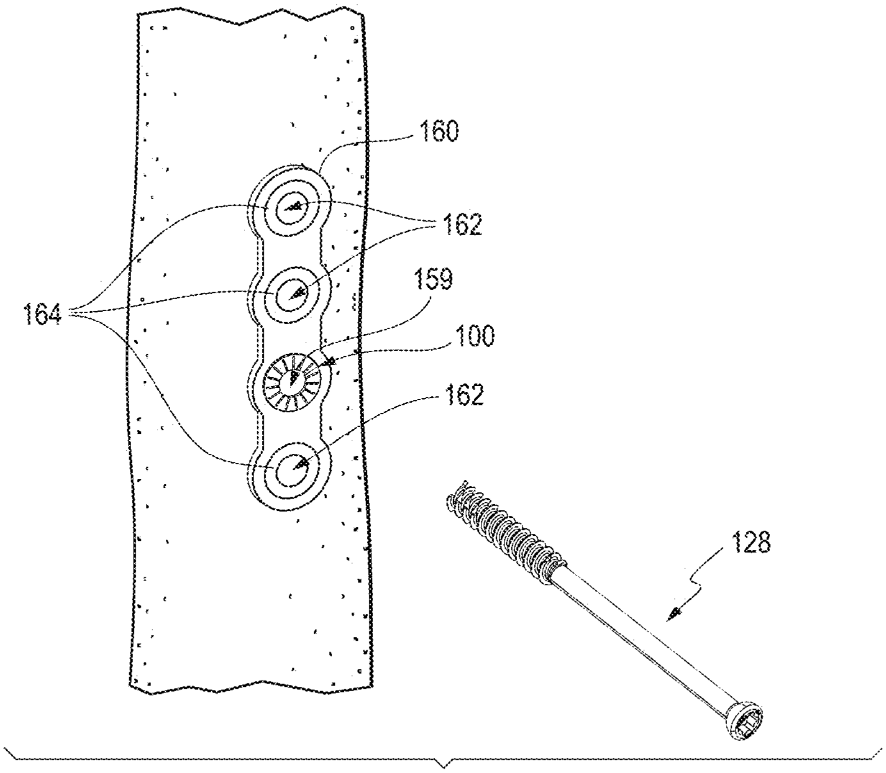
FIG. 14 is perspective view of the surgical region as shown in FIG. 13 illustrating the plate disposed on the bone and the compression device received in an opening of the bone plate.
Figure 15:
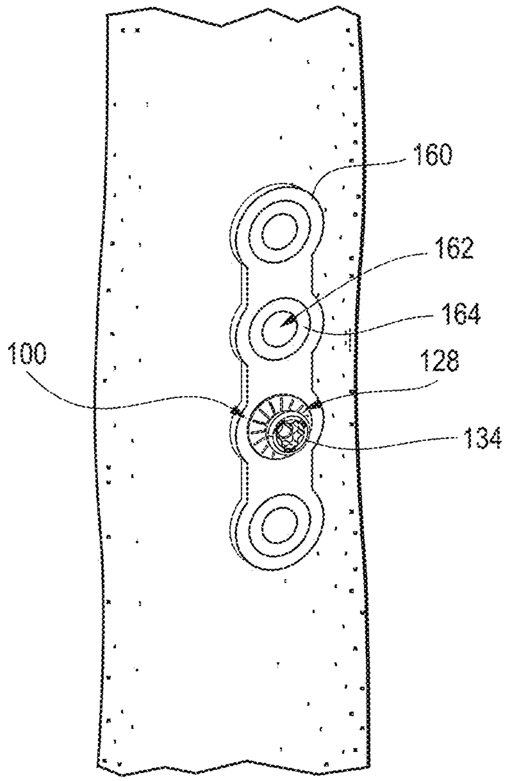
FIG. 15 is a perspective view depicting the surgical region as shown in FIGS. 13 and 14 after installation of the bone screw and compression of the compression device.

As indicated above, the compression device 100 provided herein may also be used in connection with a bone plate 160 as shown in FIGS. 13-15. Referring now to FIG. 13, the relative positioning of screw 128, the compression device 100, bone plate 160, and a bone segment are shown. A pilot hole 159 has been pre-drilled into the bone segment, and in some embodiments, may be drilled in connection with a guide wire and cannulated drill bit as described above. In some forms, the bone segment may have a fracture extending through a portion thereof. The bone plate 160 includes one or more openings 162 for receiving bone screws 128 therethrough to couple the bone plate 160 to the bone segment. In some forms, the compression device 100 may be sized to be at least partially received in a recessed portion 164 of the openings 162 of the bone plate 160. Additionally or alternatively, the compression device 100 and the openings 162 of the bone plate 160 may include mating structures to align and secure the compression device 100 therein.

In FIG. 14, the bone plate 160 has been positioned immediately adjacent the bone segment and the compression device 100 is shown seated in the recessed portion 164 of the opening 162. Thereafter, as shown in FIG. 15, the bone screw 128 may be advanced through the compression device 100 and into the pilot hole 159, through the opening 162 of the bone plate 160. The head portion 134 of the screw 128 is shown impinging upon, and compressing, the superelastic resilient teeth 110 of the compression device 100 while the teeth 110 exert an axial biasing force against the head portion 134. As illustrated, the compressed teeth 110 of the compression device 100 are in a flat configuration due to impingement of the head portion of the screw. In other forms, the teeth 110 of the compression device 100 may be compressed further into a concave configuration depending on the shape of the opening 162 and recessed portion 164 of the bone plate 160, as described in further detail above with respect to FIGS. 10-12.

Figure 16:
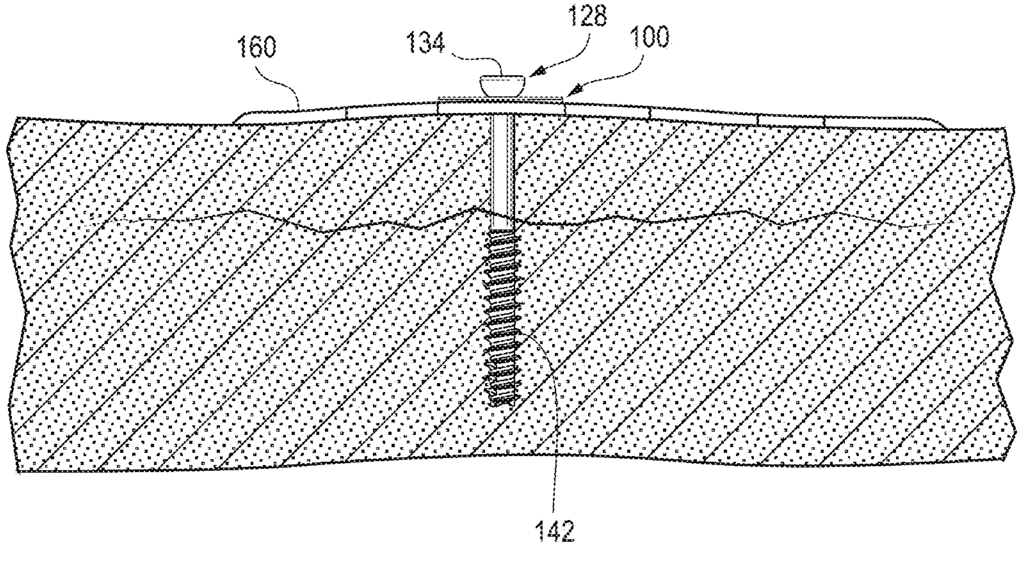
FIG. 16 is a cross-sectional view of a bone section of a patient with a bone plate, compression device, and bone screw illustrating deformation of the compression device via impingement of the head of the bone screw.

FIG. 16 depicts a bone plate 160 positioned between the compression device 100 and the surface of the bone. The threaded distal portion 142 of the screw 128 has been inserted through the opening 108 of the compression device 100 and opening 162 of the bone plate 160, and into the far portion of the bone. As shown, the screw 128 is compressing the two fractured portions of bone. In addition, the resilient teeth 110 of the compression device 100, compressed into the flat configuration, exert an axial biasing force on the head portion 134 of the screw 128.

Figure 17:
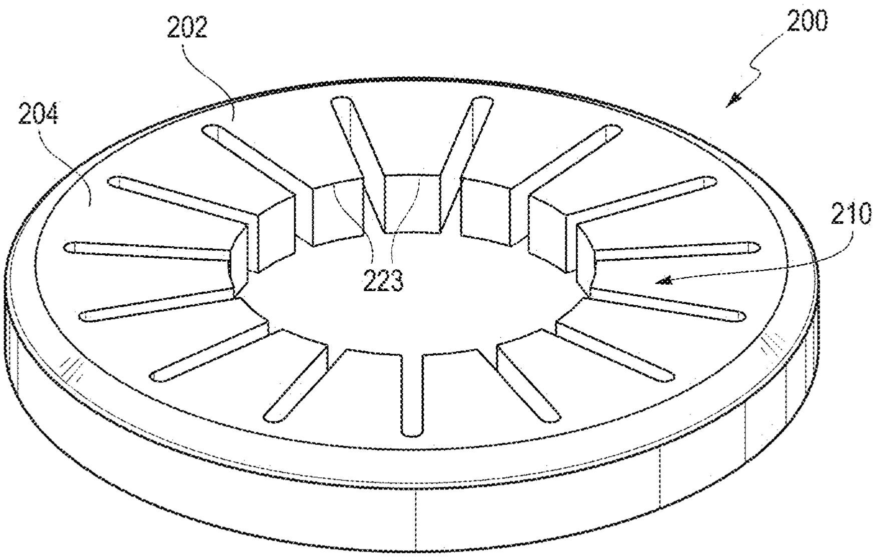
FIG. 17 is a perspective view of an alternative compression device.

Referring now to FIG. 17, an alternative compression device 200 having a substantially flat configuration in its resting state, unlike the convex compression device 100 illustrated in FIGS. 1-3. In other words, the compression device 200 is of a flat configuration when there is no force acting upon the superelastic, resilient teeth 210 thereof. As shown, the tip portion 223 of the teeth 210 does not extend proximally beyond the upper surface 204 of the peripheral portion 202 or distally beyond the lower surface of the peripheral portion 202. In such embodiments, the compression device 200 may be installed in a countersunk portion of bone, or a bone plate positioned adjacent the bone, such that the teeth 210 may be impinged upon and compressed by the head portion of a fastener such as bone screw 128.

Figure 18:
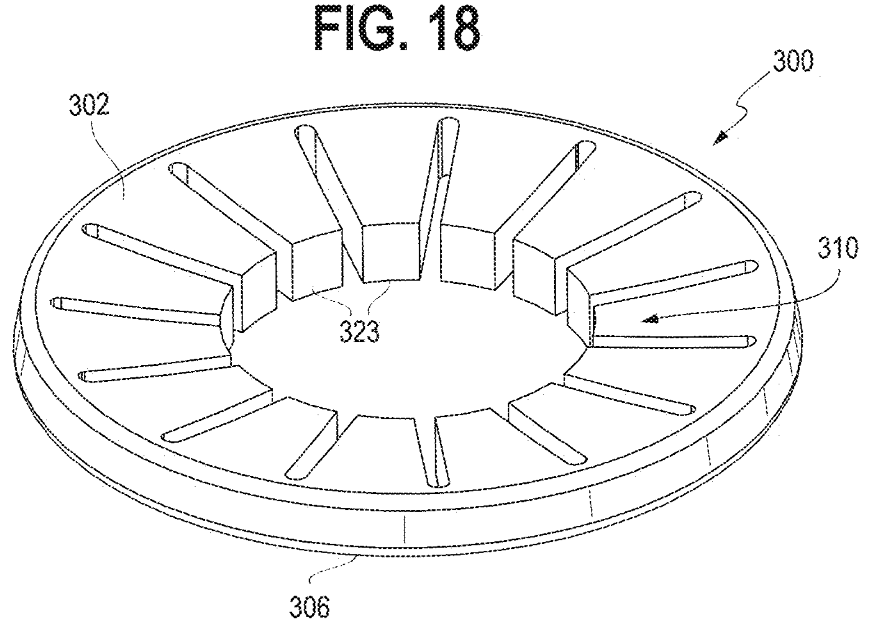
FIG. 18 is a perspective view of another alternative compression device.

FIG. 18 illustrates yet another embodiment of a compression device 300 having a substantially bowl-shaped or concave configuration in its resting state. So configured, the compression device 300 is in a concave configuration when there is no force acting upon the superelastic, resilient teeth 310 thereof. In other words, the tip portion 323 of the teeth 310 extends distally beyond the lower surface 306 of the peripheral portion 302. In such embodiments, the compression device 300 may be installed in a countersunk portion of bone, or a bone plate positioned adjacent the bone, such that the teeth 310 may be impinged upon and compressed by the head portion of a fastener such as bone screw 128.

Figure 19:
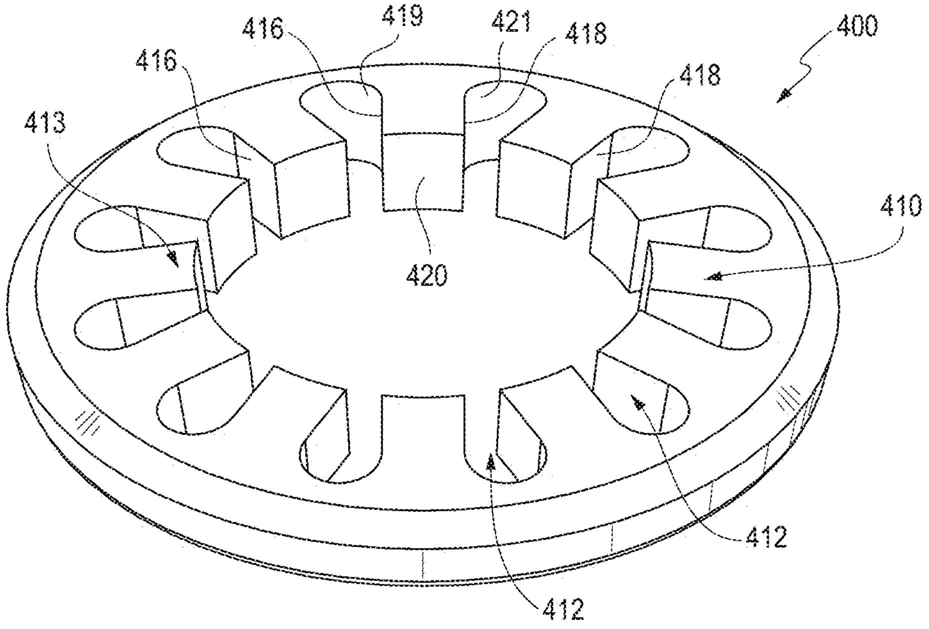
FIG. 19 is a perspective view of another alternative compression device.
Figure 20:
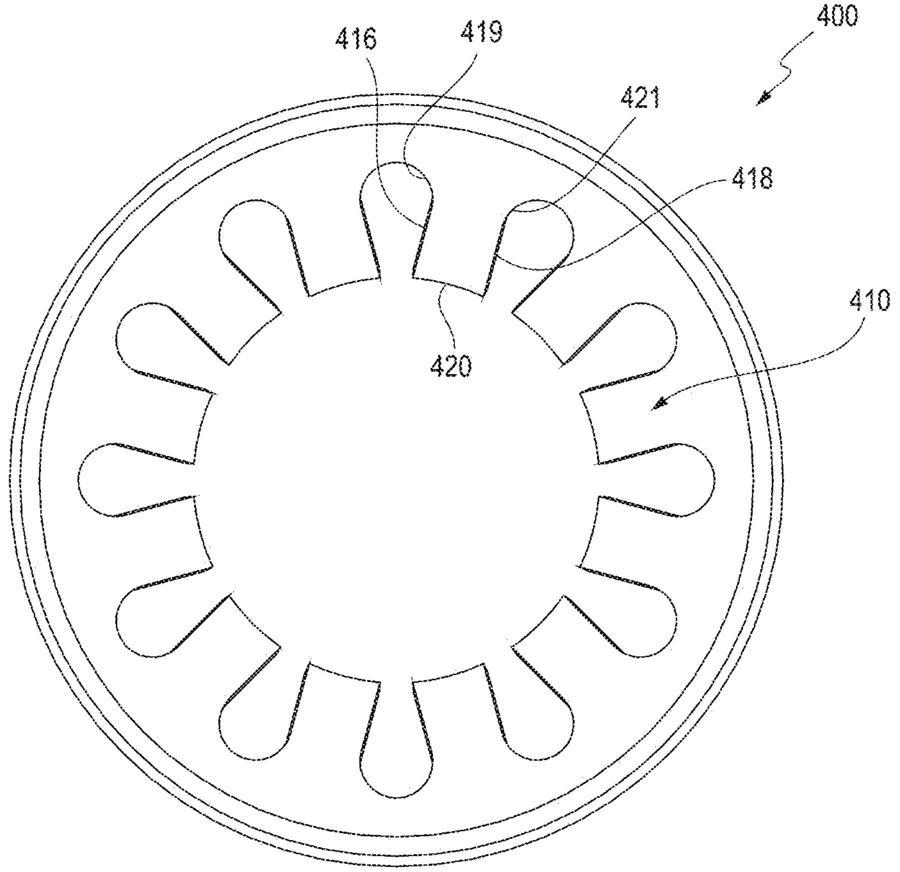
FIG. 20 is a top plan view of the compression device shown in FIG. 19.

As shown in FIGS. 19 and 20, alternatively a compression device 400 includes a plurality of teeth 410 that are shaped differently from the plurality of teeth 110, and therefore define gaps 412 having different shapes than the gaps 112. As shown, each tooth 412 has a cuboid projecting portion 413 with a first side edge 416, second side edge 418, and terminal side edge 420. Cusps 419, 421 are likewise of a different shape. As illustrated, teeth 410 define gaps 412 that have a curved surface 421. Compression device 400 is of a convex configuration and the teeth 410 are configured to exert a biasing force in an axial direction when deformed in an opposing axial direction. The compression device 400 can also be positioned in a countersunk hole in a portion of bone, or used in connection with a bone plate such as bone plate 160.

Figure 21:
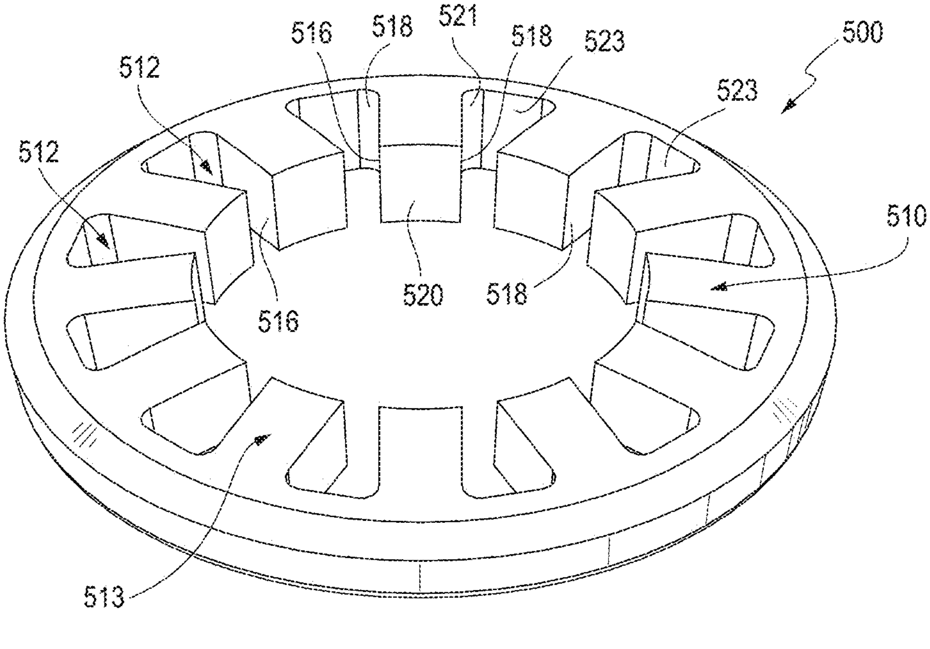
FIG. 21 is a perspective view of yet another alternative compression device.
Figure 22:
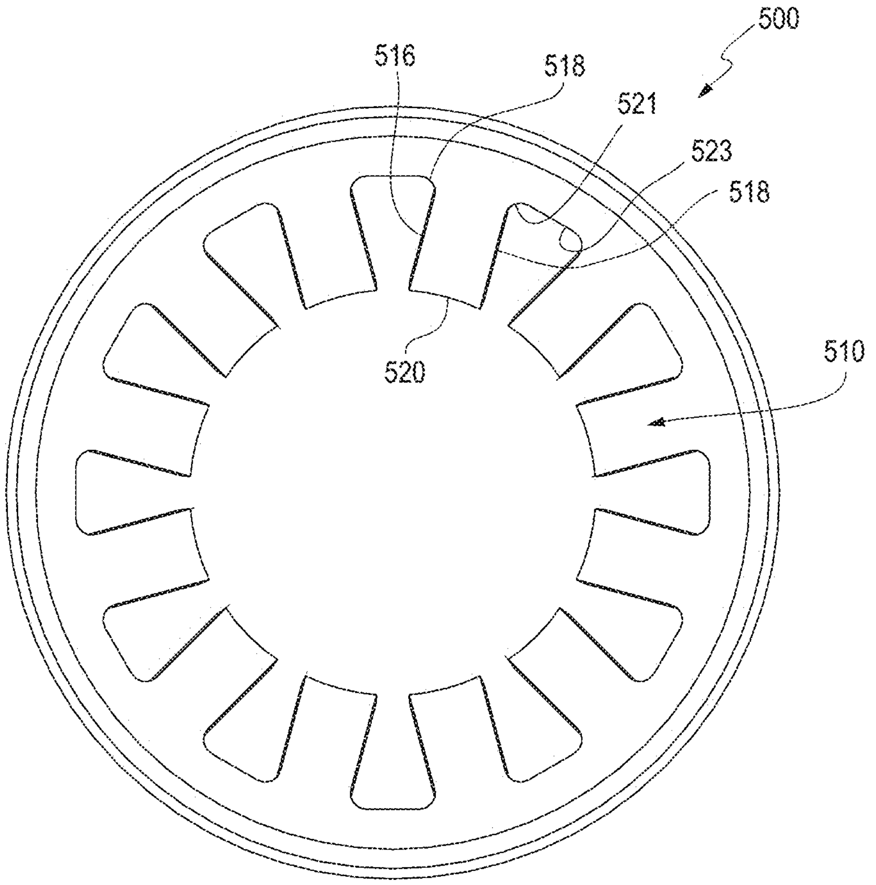
FIG. 22 is a top plan view of the compression device shown in FIG. 21.

As shown in FIGS. 21 and 22, compression device 500 includes teeth 510 that define gaps 512 having different shapes from the gaps 112. As shown, each tooth 512 has a cuboid projecting portion 513 with a first side edge 516, second side edge 518, and terminal side edge 520. As illustrated, the first and second side edges 516, 518 define gaps 512 terminate in a generally flat region 523. Cusps 519, 521 are likewise of a different shape. Compression device 500 is of a convex configuration and the teeth 510 are configured to exert a biasing force in an axial direction when deformed in an opposing axial direction.

Figure 23:
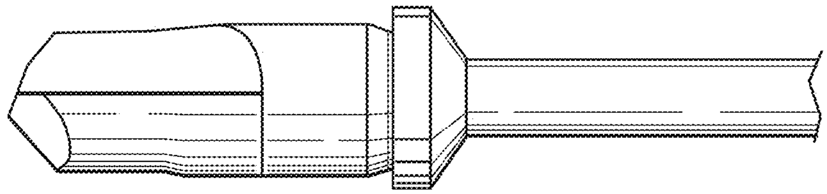
FIG. 23 illustrates a countersink in the form of a drill or drill bit.

FIG. 23 illustrates a countersink tool showing a drill bit that may be used to cut a countersunk bore in a surface of a bone segment. Such a countersink tool may be provided in connection with one or more compression devices within a kit, as described above. The size of the drill bit of the countersink tool may be selected such that the countersunk bore drilled thereby is sized to at least partially receive the compression device 100 (e.g., the resilient teeth 110) within. In some forms, different size drill bits or different countersink tools may be selected depending on the surgical indication or depending on the diameter of the compression device employed.

Although the illustrated example in FIGS. 4-7 depicts a subtalar fusion using a lag-type screw 128, the compression device 100 provided herein may be used in a variety of orthopedic applications. Such a compression device 100 could be provided for use in connection with other fasteners to stabilize any fracture or joint, and the usage is not limited to the example procedures described herein. For example, the compression device 100 may be used in connection with a cannulated screw for hip fracture repair, among other indications. The fastener in the form of threaded screw 128 may alternatively be a fully threaded bone screw, and the method of installation thereof may include drilling pilot hole having a larger diameter than the threads of the bone screw in a near bone segment, and a pilot hole having a narrower diameter than the threads of the bone screw in a far bone segment, such that compression may be likewise be achieved therebetween.

It is thus seen that a compression device configured as described herein can assist in maintaining compression between bone segments or in a bone fracture, as can the disclosed kit and methods.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A method comprising:

providing a fastener having a head portion and a shaft portion, said fastener comprising an osseointegrating material;

providing a compression device, the compression device comprising:

a peripheral portion having an upper surface, a lower surface, and a central opening; and an inwardly projecting resilient tooth;

wherein the compression device comprises a material that is superelastic at human body temperatures, and wherein the resilient tooth is configured to be deformed in an axial direction upon advancement of the fastener and impingement of the fastener against the tooth, the tooth configured to exert a biasing force against the head portion of said fastener in an opposing axial direction when so deformed;

wherein the tooth includes a tip portion extending proximally beyond the upper surface of the peripheral portion, and wherein the tooth may be deformed to an extent such that the tip portion no longer extends proximally beyond the upper surface of the peripheral portion;

surgically exposing a bone segment of a patient;

inserting the fastener through the central opening of the compression device;

advancing said fastener into said bone segment to impinge the head portion of said fastener onto the tooth of said compression device, wherein said tooth is deformed by the head portion of the fastener and thereby exerts a biasing force against the head portion of said fastener;

wherein the peripheral portion of the compression device comprises a generally annular ring portion; and and wherein the compression device comprises a plurality of inwardly projecting resilient teeth, the teeth configured to exert a biasing force in an axial direction when deformed in an opposing axial direction.

2. The method of claim 1, wherein the superelastic material is a nitinol material.

3. The method of claim 1, wherein the superelastic material is also superelastic at 25° C.

4. The method of claim 1, each of the teeth having a tip portion extending proximally beyond the upper surface of the peripheral portion, and wherein the teeth are spaced apart sufficiently such that each tooth may be deformed to an extent such that the tip portions no longer extend proximally beyond the upper surface of the peripheral portion.

5. The method of claim 1, wherein said bone segment is a fractured bone segment, and wherein said fastener is advanced through one or more portions of the fractured bone segment to repair a fracture thereof.

6. The method of claim 1, wherein said fastener is advanced through two or more bone segments to join the two or more bone segments to one another.

7. The method of claim 1, wherein the fastener comprises a lag-type bone screw.

8. The method of claim 1, further comprising:

cutting a countersink in the bone segment sized to at least partially receive the compression device and at least a portion of the head portion of the fastener; and positioning the compression device at least partially within the countersink.

9. The method of claim 1, further comprising:

providing a bone plate including a plurality of openings, wherein at least one of the openings is sized to seat the compression device therein;

positioning the bone plate proximate the bone segment;

positioning said compression device proximal said bone plate, said bone plate being positioned between said compression device and said bone segment; and inserting the fastener through the central opening of the compression device and through the at least one opening of the bone plate.

* * * * *